(12) United States Patent
Bach et al.

(10) Patent No.: US 12,611,245 B2
(45) Date of Patent: Apr. 28, 2026

(54) ELECTRODE DEVICE FOR BLOCKING OR CONTROLLING NERVES IN BODY

(71) Applicant: DEEPQURE INC., Seoul (KR)

(72) Inventors: Du Jin Bach, Seongnam-si (KR); Seok Hyeon Jo, Namyangju-si (KR)

(73) Assignee: DEEPQURE INC., Seoul (KR)

( * ) Notice: Subject to any disclaimer, the term of this patent is extended or adjusted under 35 U.S.C. 154(b) by 269 days.

(21) Appl. No.: 18/578,922

(22) PCT Filed: Jul. 16, 2021

(86) PCT No.: PCT/KR2021/009192
§ 371 (c)(1),
(2) Date: Jan. 12, 2024

(87) PCT Pub. No.: WO2023/286892
PCT Pub. Date: Jan. 19, 2023

(65) Prior Publication Data
US 2024/0315757 A1 Sep. 26, 2024

(30) Foreign Application Priority Data
Jul. 13, 2021 (KR) ........................ 10-2021-0091638

(51) Int. Cl.
*A61B 18/14* (2006.01)
*A61B 18/00* (2006.01)
(52) U.S. Cl.
CPC .... *A61B 18/14* (2013.01); *A61B 2018/00059* (2013.01); *A61B 2018/00172* (2013.01);
(Continued)
(58) Field of Classification Search
CPC . A61B 18/14; A61B 18/1482; A61B 18/1402; A61B 18/1492; A61B 18/1445;
(Continued)

(56) References Cited

U.S. PATENT DOCUMENTS 5,964,756 A * 10/1999 McGaffigan ....... A61B 18/1485
606/41
11,020,170 B2 * 6/2021 Boudreaux ........ A61B 18/1442
(Continued)

FOREIGN PATENT DOCUMENTS

EP 1 402 821 A2 3/2004
JP 201876954 A 5/2018
(Continued)

OTHER PUBLICATIONS

International Search Report of PCT/KR2021/009192 dated Apr. 8, 2022, 5 pages.
(Continued)

*Primary Examiner* — Thomas A Giuliani
(74) *Attorney, Agent, or Firm* — Merchant & Gould P.C.

(57) ABSTRACT

An electrode apparatus for nerve denervation or modulation in vivo includes a main body including a shaft; an electrode unit formed to be drawn out from one end of the shaft and configured to denervate or modulate at least some of nerves on a tube in the body; an electrode guide including a plurality of joint units and a wire connecting the plurality of joint units to each other and configured to guide the electrode unit; and a driving unit located inside the main body and configured to drive the joint units and the wire to protrude from the one end of the shaft. The driving unit drives the joint units in conjunction with the wire to have different displacements by using a gear ratio between two rack gears depending on a pitch circle diameter ratio between two pinion gears.

10 Claims, 7 Drawing Sheets

100

(52) U.S. Cl.

CPC .............. *A61B 2018/00196* (2013.01); *A61B 2018/00434* (2013.01); *A61B 2018/00577* (2013.01); *A61B 2018/00922* (2013.01); *A61B 2018/142* (2013.01)

(58) Field of Classification Search

CPC .......... A61B 2018/00172; A61B 2018/00196; A61B 2018/00434; A61B 2018/00577; A61B 2018/142; A61B 2018/00541; A61B 2018/1475; A61B 2018/0016; A61B 2018/00952; A61B 2018/1407; A61N 1/0556

USPC .......... 606/41, 45–52; 607/98, 99, 101, 113, 607/115, 116

See application file for complete search history.

(56) References Cited

U.S. PATENT DOCUMENTS

| | | | |
|---|---|---|---|
| 2007/0068990 A1* | 3/2007 | Shelton | ............ A61B 17/07207 227/175.1 |
| 2009/0171159 A1 | 7/2009 | Jorgensen et al. | |
| 2012/0330301 A1* | 12/2012 | Pellegrino | .......... A61B 17/8811 606/41 |
| 2013/0110145 A1 | 5/2013 | Weitzman | |
| 2014/0324015 A1* | 10/2014 | Romoscanu | ...... A61M 25/0147 604/95.05 |
| 2015/0141810 A1 | 5/2015 | Weadock | |
| 2017/0000511 A1 | 1/2017 | Maeng et al. | |
| 2017/0056028 A1* | 3/2017 | Germain | ............ A61B 18/1206 |
| 2018/0368914 A1 | 12/2018 | Cheng et al. | |
| 2023/0107208 A1* | 4/2023 | Lenker | ............... A61B 17/3478 700/245 |
| 2023/0157747 A1 | 5/2023 | Jeong et al. | |

FOREIGN PATENT DOCUMENTS

| | | |
|---|---|---|
| KR | 10-2015-0132899 A | 11/2015 |
| KR | 10-2016-0007087 A | 1/2016 |
| KR | 10-1590005 B1 | 1/2016 |
| KR | 10-2016-0088393 A | 7/2016 |
| KR | 10-2017-0058964 A | 5/2017 |
| KR | 10-2018-0094955 A | 8/2018 |
| KR | 10-2244131 B1 | 4/2021 |

OTHER PUBLICATIONS

Brazilian Office Action received for BR Application No. BR112024000503-8 on Jul. 16, 2021, 8 pgs.

* cited by examiner

230

ELECTRODE DEVICE FOR BLOCKING OR CONTROLLING NERVES IN BODY

CROSS REFERENCE TO RELATED APPLICATION(S)

This application is a 35 U.S.C. § 371 National Phase Entry Application from PCT/KR2021/009192, filed on Jul. 16, 2021, which claims the benefits of priority to Korean Patent Application No. 10-2021-0091638, filed on Jul. 13, 2021, the disclosures of which are herein incorporated by reference in their entirety.

TECHNICAL FIELD

The present disclosure relates to an electrode device for nerve denervation or modulation in vivo.

BACKGROUND

A denervation is a surgical procedure intended to control an abnormally overactive autonomic nervous system by damaging specific nerves. For example, a renal denervation can treat hypertension and heart diseases by damaging renal sympathetic nerves directed to the kidney, and a pulmonary denervation can treat lung diseases by damaging parasympathetic nerves directed to the lung.

Nerves usually enclose the outer walls of tubes, such as blood vessels, bronchial tubes, etc., and it may be necessary to enclose the outer walls of tubes to measure signals from the nerves or transmit electrical impulses or various energies to the nerves to damage or destroy the nerves. For example, when a surgical procedure is performed on the renal artery, the main renal artery which is a procedure target has a diameter of from 5 mm to 7 mm, and the accessory renal artery having a diameter of from 1 mm to 2 mm may also be a procedure target. Also, the artery with distributed nerves varies in size from person to person and has different sizes depending on the location.

When the surgical procedure is performed as described above, it is important to delicately locate a component including an electrode to be formed at the end of a catheter so as to enclose the outer wall of the artery. Specifically, in order to effectively denervate or modulate the nerves, the component needs to enclose the outer wall of the artery with distributed nerves in a circumferential direction. Also, it is necessary to reliably and rapidly enclose the artery with the component including the electrode.

DISCLOSURE OF THE INVENTION

Problems to be Solved by the Invention

The present disclosure is conceived to provide an electrode device having a component that guides a plurality of unit elements to sequentially protrude and an electrode to enclose the circumference of a tube in the body.

Also, the present disclosure is conceived to provide an electrode device configured such that an operation of protruding a plurality of unit elements is performed in conjunction with an operation of setting a path for the plurality of unit elements.

Further, the present disclosure is conceived to provide an electrode device in which a component connected to a plurality of unit elements and configured to guide an electrode is manufactured as a single member without assembly.

The problems to be solved by the present disclosure are not limited to the above-described problems. There may be other problems to be solved by the present disclosure.

Means for Solving the Problems

According to an aspect of the present disclosure, an electrode device for nerve denervation or modulation in vivo includes a main body including a shaft; an electrode unit formed to be drawn out from one end of the shaft and configured to denervate or modulate at least some of nerves on a tube in the body; an electrode guide including a plurality of joint units and a wire connecting the plurality of joint units to each other and configured to guide the electrode unit; and a driving unit located inside the main body and configured to drive the joint units and the wire to protrude from the one end of the shaft. The driving unit drives the joint units in conjunction with the wire to have different displacements by using a gear ratio between two rack gears depending on a pitch circle diameter ratio between two pinion gears.

According to the present disclosure, the driving unit includes a motor unit; a rod block including a rod of which one end is connected to the joint units and which is moved in the forward and backward directions by means of the motor unit; and a wire block configured to support wire and move in the forward and backward directions in parallel to the rod block. The rod block is moved in the forward direction, a distance between the rod block and the wire block increases, and when the rod block is moved in the backward direction, the distance between the rod block and the wire block decreases.

According to the present disclosure, the driving unit includes a rod block of which one end is connected to the joint units and which is moved in forward and backward directions; a wire block configured to support the wire and moved in the forward and backward directions; and a variable connection unit including the two pinion gears and the two rack gears corresponding to the two pinion gears and configured to connect the rod block and the wire block to each other and vary a distance between the rod block and the wire block.

According to the present disclosure, the two rack gears includes a rod rack fixed to the rod block and a wire rack fixed to the wire block, the two pinion gears includes a rod pinion that converts rectilinear movement of the rod rack into rotational movement and a wire pinion that forms rectilinear movement of the wire rack while rotating with the rod pinion, and the rod pinion and the wire pinion are coaxially rotated around a fixed pinion shaft.

According to the present disclosure, the rod pinion has a greater pitch circle diameter than the wire pinion.

According to the present disclosure, the wire is protruded from one end of the shaft with a smaller displacement than the joint units and provides a force of pulling the joint units in a direction to be wound around the tube.

According to the present disclosure, each joint unit includes a hinge unit formed on one or both sides of the joint unit in a longitudinal direction to be connected to an adjacent joint unit; and a wire hole formed to allow insertion of the wire at a location spaced apart from a rotation center of the hinge unit.

According to the present disclosure, each joint unit includes a hinge unit formed on one or both sides of the joint unit in a longitudinal direction to be connected to an adjacent joint unit; and a winding support unit formed on one or both sides of the joint unit in the longitudinal direction to support the adjacent joint unit. Since adjacent joint units are supported by means of the winding support unit, a force of supporting the joint units is provided to the joint units in an opposite direction to a direction to be wound around the tube.

According to the present disclosure, the electrode guide further includes a tip joint connected to the end of the plurality of joint units connected sequentially to each other and coupled to ends of the electrode unit and the wire, respectively.

According to the present disclosure, the plurality of joint units is made of an elastically deformable material and formed as one body, and a winding support groove of which at least a part of a space is deformed to be closed by a force of the wire is formed between adjacent joint units of the electrode guide.

The above-described aspects are provided by way of illustration only and should not be construed as liming the present disclosure. Besides the above-described embodiments, there may be additional embodiments described in the accompanying drawings and the detailed description.

Effects of the Invention

According to an electrode device of the present disclosure, a plurality of joint units operates in conjunction with a wire by means of a driving unit, and, thus, an electrode guide protrudes from a shaft and operates to enclose a tube. Accordingly, a space where the electrode guide operates can be minimized. Therefore, an operation of denervating or modulating nerves can be performed safely and accurately in a narrow space. Since the wire is driven in conjunction with the joint units to have different displacements by means of the driving unit, the electrode guide can be drawn out and changed in location accurately and simply.

Further, according to the electrode device of the present disclosure, the joint units can be operated by means of a motor unit and a rod block, and the wire can be operated by means of a wire block variably connected to the rod block. That is, an operation of protruding the electrode guide and an operation of controlling the location of the electrode guide can be performed together by means of the single motor unit, and, thus, it is possible to efficiently perform a precise operation.

Meanwhile, according to the electrode device of the present disclosure, the electrode guide including the plurality of joint units as one body is formed while implementing driving of the plurality of joint units. Thus, the electrode device can be manufactured through a simple process and produced in a small size, which results in a reduction in manufacturing cost.

BEST MODE FOR CARRYING OUT THE INVENTION

Figure 1:
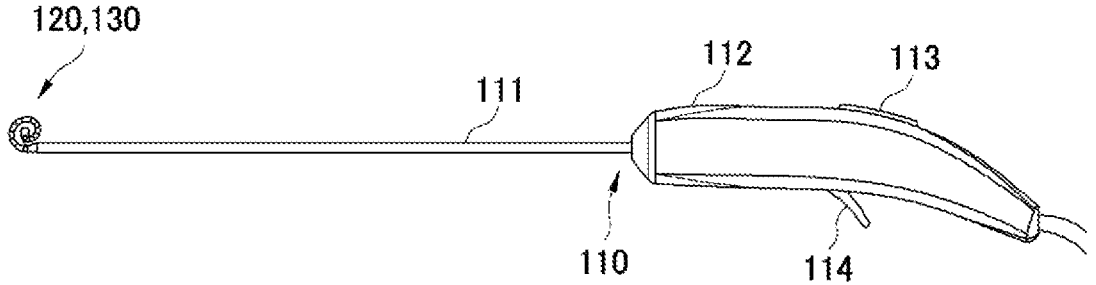
FIG. 1 is a side view of an electrode device according to an embodiment of the present disclosure.

Hereafter, example embodiments will be described in detail with reference to the accompanying drawings so that the present disclosure may be readily implemented by those skilled in the art. However, it is to be noted that the present disclosure is not limited to the example embodiments but can be embodied in various other ways. In the drawings, parts irrelevant to the description are omitted for the simplicity of explanation, and like reference numerals denote like parts through the whole document.

Through the whole document, the term "connected to" or "coupled to" that is used to designate a connection or coupling of one element to another element includes both a case that an element is "directly connected or coupled to" another element and a case that an element is "electronically connected or coupled to" another element via still another element. Further, it is to be understood that the term "comprises or includes" and/or "comprising or including" used in the document means that one or more other components, steps, operation and/or existence or addition of elements are not excluded in addition to the described components, steps, operation and/or elements unless context dictates otherwise and is not intended to preclude the possibility that one or more other features, numbers, steps, operations, components, parts, or combinations thereof may exist or may be added. Through the whole document, the term "on" that is used to designate a position of one element with respect to another element includes both a case that the one element is adjacent to the other element and a case that any other element exists between these two elements.

Figure 2:
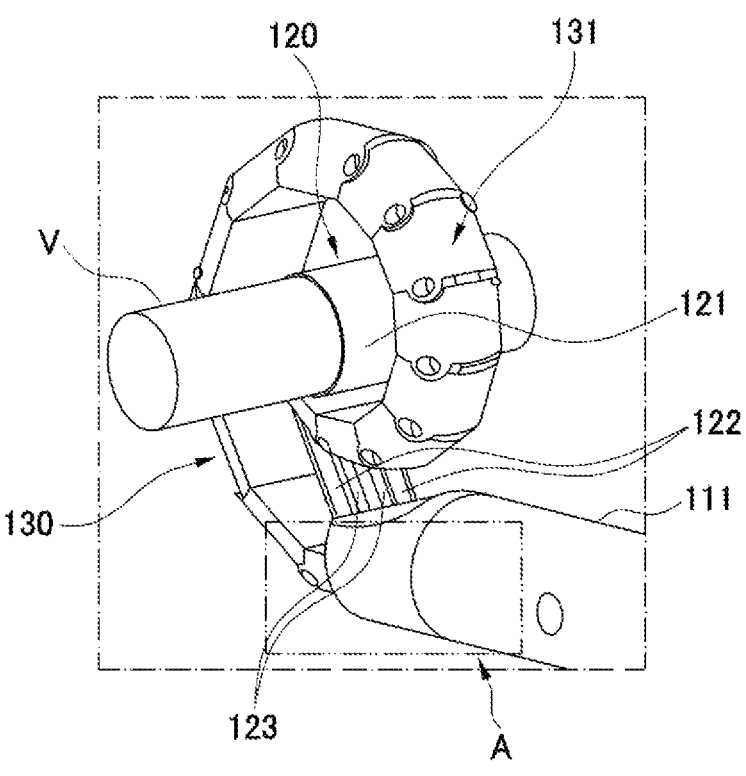
FIG. 2 illustrates a state where an electrode guide illustrated in FIG. 1 guides and locates an electrode unit to enclose a blood vessel according to an embodiment of the present disclosure.
Figure 3:
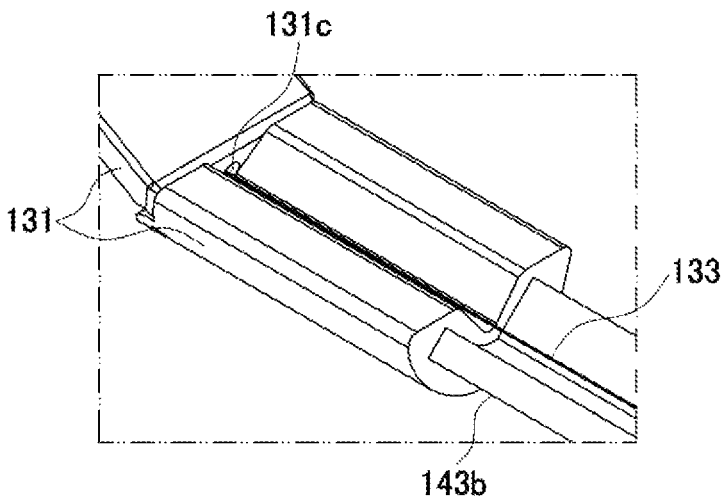
FIG. 3 illustrates components inside a shaft in an area A illustrated in FIG. 2.
Figure 4:
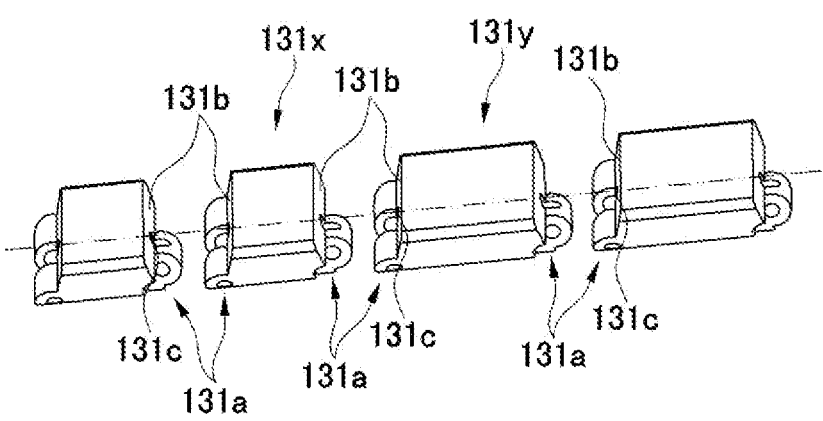
FIG. 4 is an exploded perspective view illustrating a portion of joint units illustrated in FIG. 2.
Figure 5:
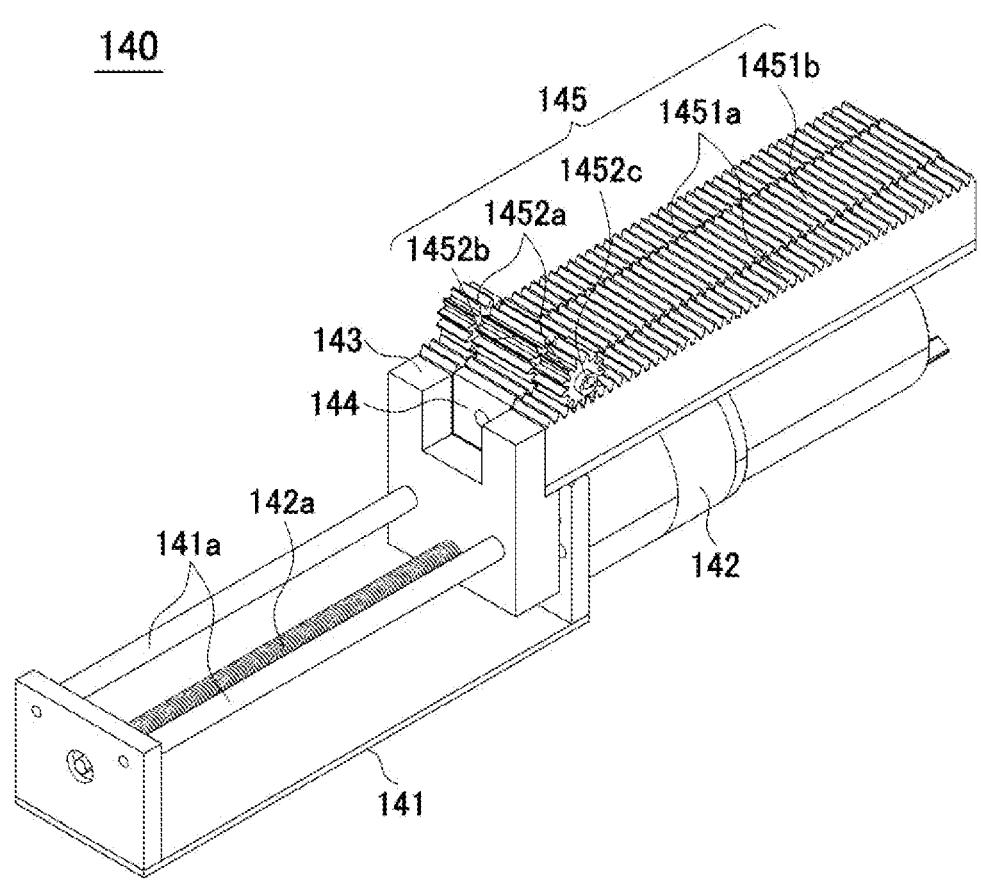
FIG. 5 is an exploded perspective view of a driving unit located inside a main body illustrated in FIG. 1.

FIG. 1 is a side view of an electrode device according to an embodiment of the present disclosure. FIG. 2 illustrates a state where an electrode guide illustrated in FIG. 1 guides and locates an electrode unit to enclose a blood vessel according to an embodiment of the present disclosure. FIG. 3 illustrates components inside a shaft in an area A illustrated in FIG. 2. FIG. 4 is an exploded perspective view illustrating a portion of joint units illustrated in FIG. 2. FIG. 5 is an exploded perspective view of a driving unit located inside a main body illustrated in FIG. 1.

Figure 6A:
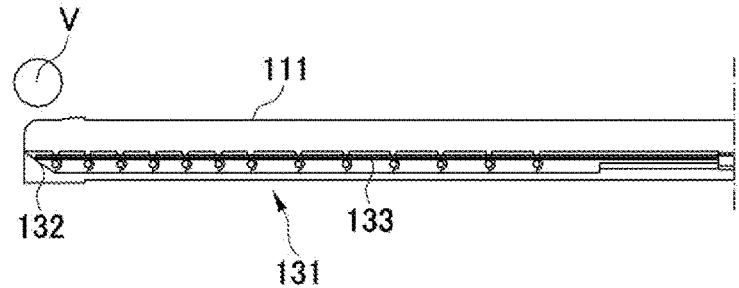
FIG. 6A illustrates an operation process of the electrode guide according to an embodiment of the present disclosure.
Figure 6B:
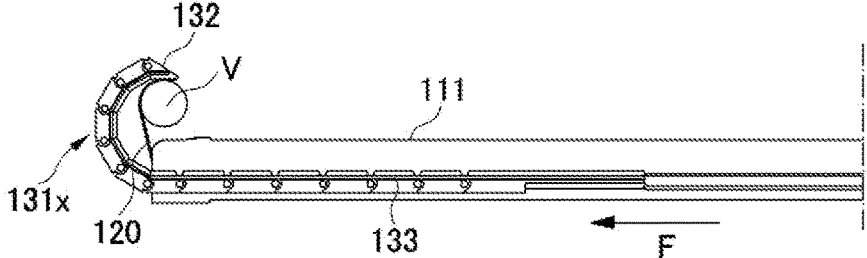
FIG. 6B illustrates an operation process of the electrode guide according to an embodiment of the present disclosure.
Figure 6C:
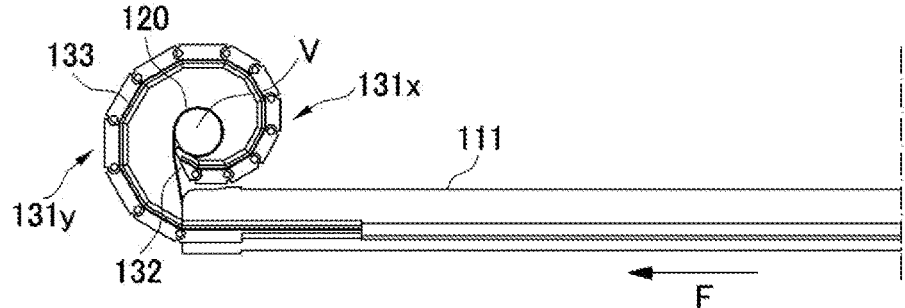
FIG. 6C illustrates an operation process of the electrode guide according to an embodiment of the present disclosure.
Figure 7A:
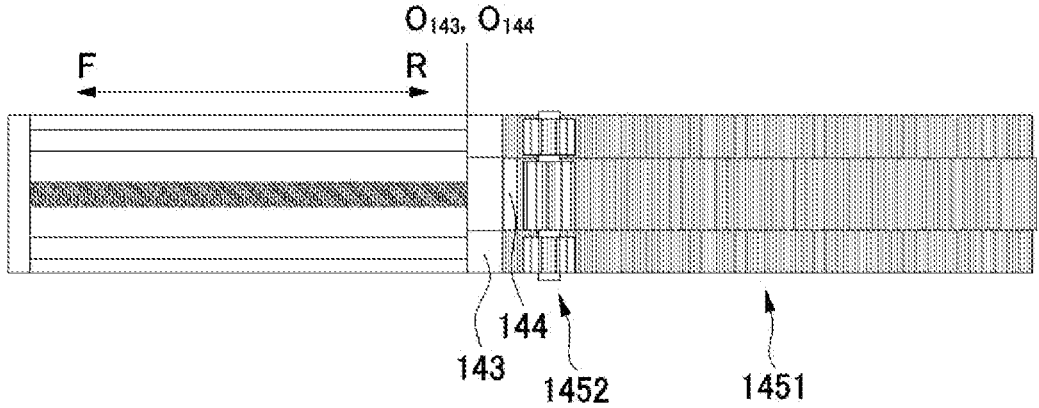
FIG. 7A is a plan view illustrating an operation process of the driving unit according to an embodiment of the present disclosure.
Figure 7B:
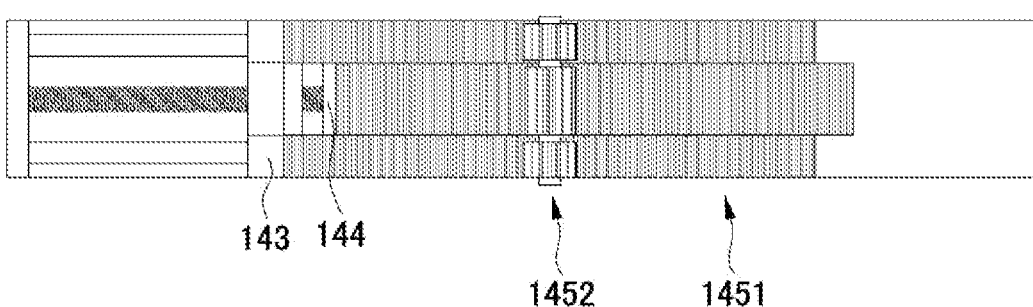
FIG. 7B is a plan view illustrating an operation process of the driving unit according to an embodiment of the present disclosure.
Figure 7C:
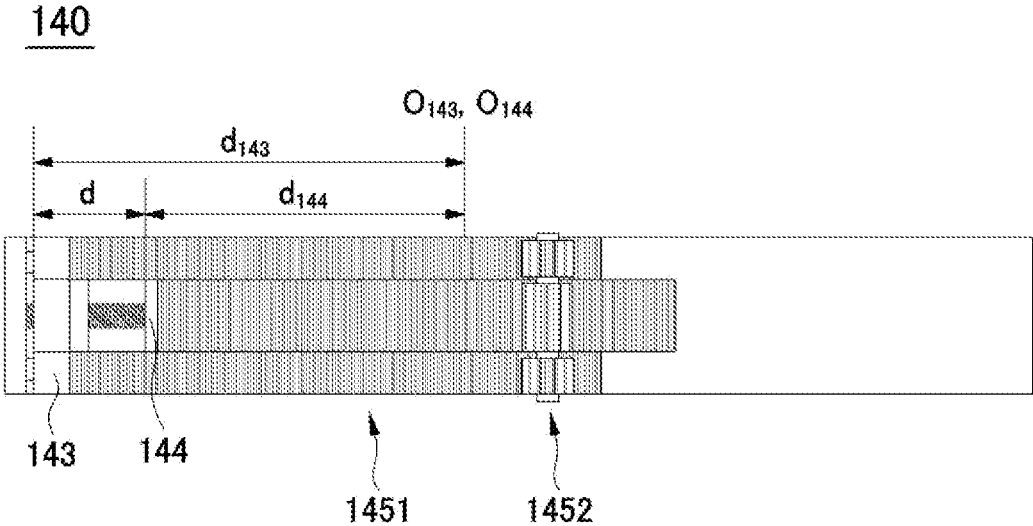
FIG. 7C is a plan view illustrating an operation process of the driving unit according to an embodiment of the present disclosure.

FIG. 6A through FIG. 6C illustrates an operation process of the electrode guide according to an embodiment of the present disclosure. FIG. 7A through FIG. 7C is a plan view illustrating an operation process of the driving unit according to an embodiment of the present disclosure.

Referring to FIG. 1, the electrode device 100 according to an embodiment of the present disclosure includes the main body 110, the electrode unit 120, the electrode guide 130 and the driving unit 140.

The main body 110 may include the shaft 111 extending in one direction, a grip portion 112 connected to the shaft 111 so as to be gripped by an operator, a guide manipulation unit 113 formed on the grip portion 112 so as to manipulate an operation of the electrode guide 130, and an electrode manipulation unit 114 formed on the grip portion 112 so as to manipulate energy transfer to the electrode unit 120. The components for driving and controlling the electrode unit 120 and the electrode guide 130 may be located inside the main body 110.

The electrode unit 120 is formed to be drawn out from one end of the shaft 111 and configured to denervate or modulate at least part of nerves distributed on a tissue in the body including a tube depending on manipulation by the operator. The electrode unit 120 is accommodated inside the shaft 111 and when the electrode device 100 of the present disclosure operates, the electrode unit 120 can be drawn out by means of the electrode guide 130 which will be described later.

Referring to FIG. 2, the electrode unit 120 may include a base portion 121, an electrode unit 122 and a sensor unit 123. In the electrode device 100 according to the present disclosure, an electrode encloses an outer surface of a tube or tube-shaped tissue V in the body and energy can be transferred through the electrode. To this end, the base portion 121 may be formed as a flexible printed circuit board (PCB).

The electrode unit 122 is formed on the base portion 121, and in the embodiment illustrated in FIG. 2, the electrode unit 122 may be composed of two electrodes extending parallel to each other on the base portion 121. In the present embodiment, the base portion 121 and the electrode unit 122 may be configured to extend in a circumferential direction and enclose the tube in the body or the like.

The electrode unit 122 may be made of a material such as stainless steel or gold, which is harmless to the human body and conducts electricity well, in order to block or denervate or control or modulate the nerves. Also, the electrode unit 122 may transfer various types of energy from an energy source generator. For example, the energy may include radio-frequency (RF) energy, electrical energy, laser energy, ultrasonic energy, high-intensity focused ultrasound energy, cryogenic energy and other heat energy.

Also, the electrode unit 122 may be implemented as a flexible PCB for transferring RF energy, a transducer for transferring ultrasonic energy or a metal electrode for transferring high-voltage energy and thus may transfer energy to damage the nerves.

Further, the sensor unit 123 may be formed on the base portion 121. For example, the sensor unit 123 may be a thermocouple that measures a temperature by contacting with the tube in the body or the like, and when neurotomy is performed with the electrode device 100 according to the present disclosure, the sensor unit 123 may monitor a temperature of a treatment site. The sensor unit 123 may be, for example, a thermocouple composed of a pair of copper and constantan. As another example, the sensor unit 123 may measure signals from the nerves on the tube.

The electrode guide 130 functions to bring the electrode unit 120 into contact with the tube in the body. The electrode guide 130 supports the electrode unit 120 and guides the electrode unit 120 to be brought into contact with the tube in the body.

Referring to FIG. 2 through FIG. 4, the electrode guide 130 of the present disclosure includes a plurality of joint units 131. The plurality of joint units 131 may form a curved winding path to enclose the circumference of the tube V in the body with the electrode unit 120 interposed therebetween. The state illustrated in FIG. 2 and FIG. 6C may be a state where the plurality of joint units 131 is completely drawn out along the curved winding path.

The electrode guide 130 may further include a tip joint 132 and a wire 133. The tip joint 132 may support the electrode unit 120 and may be coupled to the end of the plurality of joint units 131 connected sequentially to each other. The tip joint 132 may be drawn out from one end of the shaft 111 earlier than the plurality of joint units 131. As illustrated in FIG. 6C, the tip joint 132 may be located close to the tube V in the body and may have a tapered shape that gradually decreases in width or thickness toward the end in order to suppress interference with the electrode unit 120 or maximize the surface enclosing the tube in the body. The end of the electrode unit 120 may be fastened and fixed to the tip joint 132.

The wire 133 may be formed to sequentially penetrate the plurality of joint units 131. Referring to FIG. 3 and FIG. 4, each joint unit 131 may have a wire hole 131c in a longitudinal direction to allow penetration of the wire 133. The end of the wire 133 sequentially penetrating the wire holes 131c may be coupled and fixed to the tip joint 132, and the wire 133 can slide with respect to each joint unit 131 in the wire hole 131c in the longitudinal direction. Therefore, the wire 133 can guide the plurality of joint units 131 and the tip joint 132 to be located on the winding path and provide a force of pulling the plurality of joint units 131 and the tip joint 132 in a direction to be wound around the tube V.

The wire 133 may be operated to protrude from one end of the shaft 111 together with to the plurality of joint units 131. Here, the wire 133 may be designed to protrude less than the joint unit 131 and thus can provide a force of pulling the plurality of joint units 131 along a curved path.

Referring to FIG. 4, each join unit 131 may include hinge units 131a and winding support units 131b. The hinge units 131a are configured for rotatable connection to adjacent joints and may be formed on one or both sides of the joint unit 131 in the longitudinal direction in which the joint units 131 are connected parallel to each other. As illustrated in FIG. 4, the hinge unit 131a may have a rotation axis in a direction intersecting the longitudinal direction so as to be connected to the hinge unit 131a of the adjacent joint unit 131. A hinge pin (not illustrated) may be inserted into and fastened to each hinge unit 131a in the direction of the rotation axis.

The winding support units 131b are configured to support the plurality of joint units 131 on the winding path and may be formed on one or both sides of the joint unit 131 in the longitudinal direction to support the adjacent joint unit 131. As illustrated in FIG. 4, the winding support unit 131b may be located adjacent to the hinge unit 131a in an inward direction of the electrode guide 130 (in a direction of winding the joint unit 131). For example, the winding support unit 131b may be formed as a surface having a predetermined angle and area and supported by the adjacent winding support unit 131b in surface contact with each other, and, thus, a wound shape of the electrode guide 130 can be maintained. The winding support unit 131b and the wire hole 131c may be formed at locations spaced apart from a rotation center of the hinge unit 131a in an inward direction toward the tube V in the body.

When the wire 133 is pulled backwards relative to the electrode guide 130 (when a length of the wire 133 drawn out from the shaft 111 is smaller than that of the joint unit 131), a tensile force may be applied to the wire 133 in a direction of winding the electrode guide 130. On the other hand, the winding support units 131*b* may provide a force of supporting the joint units 131 to each other in a direction of suppressing winding of the electrode guide 130. Since the wire 133 and the winding support units 131*b* form a balanced force in opposite directions, the electrode guide 130 can be fixed on the winding path.

Meanwhile, as illustrated in FIG. 4, the electrode guide 130 may include a first joint group 131*x* and a second joint group 131*y*. That is, the plurality of joint units 131 may be divided into the first joint group 131*x* and the second joint group 131*y* having different lengths.

Due to a difference in length, the first joint group 131*x* may form a first radius of curvature and the second joint group 131*y* may form a second radius of curvature greater than the first radius of curvature. As can be seen from FIG. 6C, the joint units (the first joint group 131*x*) having a relatively small length may form a smaller radius of curvature and the joint units (the second joint group 131*y*) having a relatively great length may form a greater radius of curvature.

When the joint units 131 located close to the tip joint 132 form a path having a smaller radius of curvature, a path along which the tip joint 132 enters a space between the tube in the body and the shaft 111 may be formed as shown in FIG. 6C. Also, the electrode guide 130 including the joint units 131 may have an overall spiral shape.

Hereafter, the driving unit 140 of the electrode device 100 according to the present disclosure will be described.

The driving unit 140 drives the joint units 131 in conjunction with the wire 133 to have different displacements by using a gear ratio between two rack gears depending on a pitch circle diameter ratio between two pinion gears. This means that if a pitch circle diameter is 1, a movement distance of the rack gears is reduced by half, as compared to a case where the pitch circle diameter is 2.

The driving unit 140 drives the joint units 131 and the wire 133 of the electrode guide 130 so as to protrude from one end of the shaft and drives the joint units 131 in conjunction with the wire 133 to have different displacements.

For example, the wire 133 may be protruded from one end of the shaft 111 in a smaller amount (length) than the joint units 131 by means of the driving unit 140. The joint units 131 may be pulled in one direction (in a direction to be wound around the tube in the body) by means of the wire 133 as much as a difference in protruding amount and may be protruded while forming a curved winding path. More specifically, whenever the joint units 131 protrude and rotate at a winding angle (for example, 30°) Formed by the winding support units 131*b*, the wire 133 may protrude in a relatively small amount.

Referring to FIG. 6A through FIG. 6C, the electrode guide 130 is accommodated together with the electrode unit 120 inside the shaft 111 and may protrude from one end in a forward direction F while forming a winding path at the time of surgical procedure. When the plurality of joint units 131 is sequentially drawn out, the plurality of joint units 131 may move along the curved winding path due to a difference in displacement from the wire 133 and thus may overall enclose the tube V. Further, the electrode guide 130 is spaced apart from an outer circumferential surface of the tube and the electrode unit 120 located inside the wound electrode guide 130 may be in close contact with the outer circumferential surface of the tube V.

According to the present disclosure, the plurality of joint units 131 may be drawn out from the shaft 111 by means of the driving unit 140 and wound in a direction of enclosing the tube V. Accordingly, a space where the electrode guide 130 operates can be minimized, and an operation of denervating or modulating nerves can be performed safely and accurately in a narrow space.

Further, since the wire 133 is driven in conjunction with the joint unit 131 to have different displacements by means of the driving unit 140, the electrode guide 130 of the electrode device 100 according to the present disclosure can secure precision and repeatability in operation path.

Hereafter, the detailed configuration and function of the driving unit 140 will be described.

The driving unit 140 may include a frame 141, a motor unit 142, a rod block 143, a wire block 144 and a variable connection unit 145. The frame 141 may be provided to be fixed inside the main body and may include a guide slot or guide shaft 142*b* extending in forward and backward directions.

The motor unit 142 may be connected to the frame 141 and may include a rotation shaft 142*a* rotatably supported by the frame 141. For example, the motor unit 142 may receive electrical energy to rotate the rotation shaft 142*a*.

One end of the rod block 143 may be connected to the joint unit 131. The rod block 143 may be moved in the forward and backward directions by means of the motor unit 142. Specifically, the rod block 143 may be moved in the forward and backward directions in engagement with the rotation shaft 142*a* extending in the forward and backward directions and having a thread thereon. The rod block 143 may be configured to be coupled to a rod 143*b*, which is located inside the shaft 111 and extends in one direction (forward and backward directions) and supports the joint units 131, and may be configured to be slidably coupled to the guide slot or guide shaft 142*b* of the frame 141.

In addition to the above-described rotation shaft 142*a* and motor unit 142, the driving unit 140 according to the present disclosure may be configured to move the rod block 143 in the forward and backward directions by various linear actuation mechanisms. For example, the driving unit 140 may include a linear actuator of cylinder type including a pneumatic, hydraulic or electric linear actuator, or a piezoelectric or ultrasonic linear actuator.

The wire block 144 may be formed to support the wire 133 and moved in the forward and backward directions in parallel to the rod block 143 in conjunction with the rod block 143.

The variable connection unit 145 may connect the rod block 143 and the wire block 144 to each other and vary a distance between the rod block 143 and the wire block 144. To this end, the variable connection unit 145 may be provided with two rack gears 1451 and two pinion gears 1452 corresponding thereto.

Referring to FIG. 5, the two rack gears 1451 include a rod rack 1451*a* and a wire rack 1451*b*, and the rod rack 1451*a* may be coupled to the rod block 143 so as to move together. The wire rack 1451*b* may be coupled to the wire block 144 so as to move together.

The two pinion gears 1452 include a rod pinion 1452*a* and a wire pinion 1452*b*, and the rod pinion 1452*a* and the wire pinion 1452*b* may be coaxially rotated around a pinion shaft 1452*c* fixed to one inner side of the main body.

The rod rack 1451*a* corresponds to the rod pinion 1452*a*, and the wire rack 1451*b* corresponds to the wire pinion 1452*b*. A sawtooth provided at the rod rack 1451*a* may be engaged with a sawtooth provided at the rod pinion 1452*a*, and a sawtooth provided at the wire rack 1451*b* may be engaged with a sawtooth provided at the wire pinion 1452*b*.

The rod pinion 1452*a* may be formed to have a greater pitch circle diameter than the wire pinion 1452*b*. Here, when the rod pinion 1452*a* is rotated together with the wire pinion 1452*b*, a movement distance of the rod rack 1451*a* caused by rotation of the rod pinion 1452*a* may be greater than a movement distance of the wire rack 1451*b* caused by rotation of the wire pinion 1452*b*.

An embodiment of power transmission in the motor 142 will be described with reference to FIG. 5. While the rotation shaft 142*a* is rotated by means of the motor 142, the rod block 143 may move on a thread on an outer circumferential surface of the rotation shaft 142*a* along the guide shaft 142*b*. When the rod block 143 is moved, the rod rack 1451*a* fixed to the rod block 143 may be moved together and rectilinear movement of the rod rack 1451*a* may be transferred to rotational movement of the rod pinion 1452*a*. When the rod pinion 1452*a* is rotated, the wire pinion 1452*b* is rotated together around the pinion shaft 1452*c*, rotational movement of the wire pinion 1452*b* may be transferred to the wire rack 1451*b* and the wire block 144 fixed to the wire rack 1451*b* may be moved parallel to the rod block 143.

FIG. 7A through FIG. 7C illustrate states corresponding to the states illustrated in FIG. 6A through FIG. 6C, respectively. Specifically, in the state where the electrode guide 130 is located inside the shaft 111 as illustrated in FIG. 6A, the rod block 143 and the wire block 144 may be placed at respective predetermined locations $O_{143}$ and $O_{144}$ close to the motor unit 142 as illustrated in FIG. 7A. Here, the rod block 143 and the wire block 144 may be closest to each other.

When the rotation shaft 142*a* is rotated in one direction by means of the motor unit 142, the rod block 143 engaged with the rotation shaft 142*a* may move in the forward direction F as illustrated in FIG. 7B. The joint units 131 of the electrode guide 130 may be pushed by the rod connected to the rod block 143 so as to protrude from one end of the shaft 111 as illustrated in FIG. 6B. The rod block 143 may be guided in the forward direction.

Here, the wire block 144 may be moved in the forward direction along with the rod block 143 by the variable connection unit 145. When the rod block 143 is moved in the forward direction F, the wire block 144 is also moved in the forward direction. Here, a distance between the rod block 143 and the wire block 144 may gradually increase due to a gear ratio between the rod rack 1451*a* and the wire rack 1451*b* depending on a pitch circle diameter ratio between the rod pinion 1452*a* and the wire pinion 1452*b*. Since the wire block 144 lags behind relative to the rod block 143, the wire 133 is drawn out from one end of the shaft 111 with a smaller displacement than the joint units 131. Accordingly, the joint units 131 are gradually pulled and bent in a predetermined direction (in a direction to be wound around the tube in the body) by means of the wire 133.

When the rod block 143 is fully moved in the forward direction, the joint units 131 are completely drawn out as illustrated in FIG. 6C. Then, as illustrated in FIG. 7C, a movement distance $d_{144}$ of the wire block 144 and the wire 133 is smaller by a predetermined value d ($d=d_{143}-d_{144}$) than a movement distance $d_{143}$ of the rod block 143 and the joint units 131.

When the rotation shaft 142*a* of the motor unit 142 is rotated in the opposite direction, the rod block 143 may be moved in a backward direction R. As the rod block 143 is moved in the backward direction R, the distance between the rod block 143 and the wire block 144 may gradually decrease.

The wire block 144 may be moved in the forward and backward directions while the distance between the rod block 143 and the wire block 144 is varied by means of the variable connection unit 145 of the present disclosure. That is, when the rod block 143 is moved in the forward direction, the distance between the rod block 143 and the wire block 144 may gradually increase, and when the rod block 143 is moved in the backward direction, the distance between the rod block 143 and the wire block 144 may decrease.

The joint units 131 can be operated by means of the motor unit 142 and the rod block 143, and the wire 133 can be operated by means of the wire block 144 in conjunction with the rod block 143. That is, an operation of protruding the electrode guide 130 and an operation of locating the electrode guide 130 can be performed together by means of the single motor unit 142, and, thus, it is possible to effectively perform a precise operation.

Meanwhile, the electrode guide 130 can be located to fully enclose the tube in the body. Therefore, it is possible to generally denervate or modulate the nerves around the tube in a one-time surgical procedure and thus possible to increase the treatment effect.

Figure 8:
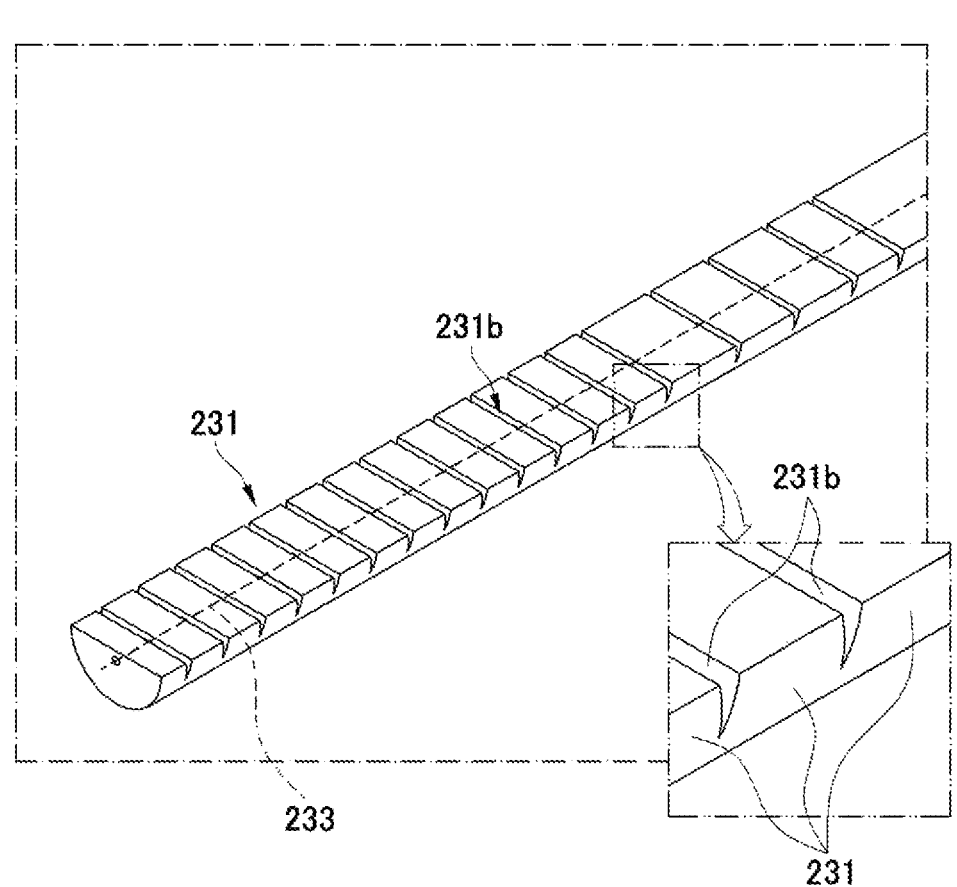
FIG. 8 is an exploded perspective view of the electrode guide according to another embodiment of the present disclosure.

FIG. 8 is a perspective view of an electrode guide 230 according to another embodiment of the present disclosure. Hereafter, an embodiment where joint units 231 of the electrode guide 230 of the present disclosure are formed as one body will be described.

The joint units 231 of the electrode guide 230 according to another embodiment of the present disclosure may be made of a material such as elastically deformable polymer, and a plurality of joint units 231 may be formed as one body, for example, a living hinge structure.

As illustrated in FIG. 8, each joint unit 231 may be formed as one body with another joint unit 231 adjacent to each other in the longitudinal direction, and a winding support groove 231*b* may be formed between the adjacent joint units 231. At least a part of a space in the winding support groove 231*b* may be reduced or closed while the joint units 231 are located on the winding path.

Specifically, the winding support groove 231*b* may be formed to be recessed in a wedge shape in the electrode guide 230's inner surface (a surface facing the electrode unit 120). When the joint units 231 protrude, side surfaces of the wedge-shaped winding support grooves 231*b* may be in contact with each other and may be supported by each other.

The electrode guide 230 according to another embodiment of the present disclosure may further include a wire 233. The wire 233 may be formed to sequentially penetrate the plurality of joint units 231. As in the above-described embodiment, a length of the wire 233 drawn out from the shaft 111 is smaller than that of the electrode guide 230, and, thus, the wire 233 can guide the electrode guide 230 to be deformed into a shape enclosing the tube and provide a force of closing and supporting at least part of the winding support grooves 231*b*.

The electrode guide 230 according to another embodiment of the present disclosure can be manufactured as one body while implementing a reliable operation of the joint units. Since it is not necessary to assemble separately manufactured joint elements, the electrode guide 230 can be manufactured through a simple process and produced in a small size, which results in a reduction in manufacturing cost.

The above description of the present disclosure is provided for the purpose of illustration, and it would be understood by a person with ordinary skill in the art that various changes and modifications may be made without changing technical conception and essential features of the present disclosure. Thus, it is clear that the above-described embodiments are illustrative in all aspects and do not limit the present disclosure.

The scope of the present disclosure is defined by the following claims rather than by the detailed description of the embodiment. It shall be understood that all modifications and embodiments conceived from the meaning and scope of the claims and their equivalents are included in the scope of the present disclosure.

We claim:

1. An electrode device for nerve denervation or modulation in vivo, comprising:

a main body including a shaft;

an electrode unit formed to be drawn out from one end of the shaft and configured to denervate or modulate at least some nerves on a tube in the body;

an electrode guide including a plurality of joint units and a wire connecting the plurality of joint units to each other and configured to guide the electrode unit; and a driving unit located inside the main body and configured to drive the joint units and the wire to protrude from the one end of the shaft, wherein the driving unit drives the joint units in conjunction with the wire to have different displacements by using a gear ratio between two rack gears depending on a pitch circle diameter ratio between two pinion gears.

2. The electrode device of claim 1, wherein the driving unit includes:

a motor unit;

a rod block including a rod of which one end is connected to the joint units and which is moved in the forward and backward directions by means of the motor unit; and a wire block configured to support wire and move in the forward and backward directions in parallel to the rod block, and wherein when the rod block is moved in the forward direction, a distance between the rod block and the wire block increases, and when the rod block is moved in the backward direction, the distance between the rod block and the wire block decreases.

3. The electrode device of claim 1, wherein the driving unit includes:

a rod block of which one end is connected to the joint units and which is moved in forward and backward directions;

a wire block configured to support the wire and moved in the forward and backward directions; and a variable connection unit including the two pinion gears and the two rack gears corresponding to the two pinion gears and configured to connect the rod block and the wire block to each other and vary a distance between the rod block and the wire block.

4. The electrode device of claim 3, wherein the two rack gears include a rod rack fixed to the rod block and a wire rack fixed to the wire block, the two pinion gears include a rod pinion that converts rectilinear movement of the rod rack into rotational movement and a wire pinion that forms rectilinear movement of the wire rack while rotating with the rod pinion, and the rod pinion and the wire pinion are coaxially rotated around a fixed pinion shaft.

5. The electrode device of claim 4, wherein the rod pinion has a greater pitch circle diameter than the wire pinion.

6. The electrode device of claim 1, wherein the wire is protruded from one end of the shaft with a smaller displacement than the joint units and provides a force of pulling the joint units in a direction to be wound around the tube.

7. The electrode device of claim 1, wherein each joint unit includes:

a hinge unit formed on one or both sides of the joint unit in a longitudinal direction to be connected to an adjacent joint unit; and a wire hole formed to allow insertion of the wire at a location spaced apart from a rotation center of the hinge unit.

8. The electrode device of claim 1, wherein each joint unit includes:

a hinge unit formed on one or both sides of the joint unit in a longitudinal direction to be connected to an adjacent joint unit; and a winding support unit formed on one or both sides of the joint unit in the longitudinal direction to support the adjacent joint unit, and since adjacent joint units are supported by means of the winding support unit, a force of supporting the joint units is provided to the joint units in an opposite direction to a direction to be wound around the tube.

9. The electrode device of claim 1, wherein the electrode guide further includes a tip joint connected to an end of the plurality of joint units connected sequentially to each other and coupled to ends of the electrode unit and the wire, respectively.

10. The electrode device of claim 1, wherein the plurality of joint units is made of an elastically deformable material and formed as one body, and wherein a winding support groove of which at least a part of a space is deformed to be closed by a force of the wire is formed between adjacent joint units of the electrode guide.

* * * * *